United States Patent
Bossenmaier et al.

(10) Patent No.: US 8,859,737 B2
(45) Date of Patent: Oct. 14, 2014

(54) ANTI-HER3 ANTIBODIES AND USES THEREOF

(75) Inventors: Birgit Bossenmaier, Seefeld (DE); Nikolaos Dimoudis, Wielenbach (DE); Thomas Friess, Diessen-Dettenhofen (DE); Guy Georges, Habach (DE); Irene Kolm, Penzberg (DE); Hans-Willi Krell, Penzberg (DE); Valeria Lifke, Penzberg (DE); Ekkehard Moessner, Kreuzlingen (CH)

(73) Assignee: Roche Glycart AG, Schlieren (CH)

( * ) Notice: Subject to any disclaimer, the term of this patent is extended or adjusted under 35 U.S.C. 154(b) by 655 days.

(21) Appl. No.: 12/971,300

(22) Filed: Dec. 17, 2010

(65) Prior Publication Data

US 2011/0171222 A1 Jul. 14, 2011

(30) Foreign Application Priority Data

Dec. 22, 2009 (EP) .................................. 09015831

(51) Int. Cl.
- *C12P 21/08* (2006.01)
- *C07K 16/32* (2006.01)
- *A61K 39/00* (2006.01)

(52) U.S. Cl.
CPC ............ *C07K 16/32* (2013.01); *A61K 2039/505* (2013.01); *C07K 2317/73* (2013.01); *C07K 2317/92* (2013.01); *C07K 2317/732* (2013.01)
USPC .................................................... 530/387.3

(58) Field of Classification Search
None
See application file for complete search history.

(56) References Cited

U.S. PATENT DOCUMENTS

| | | | |
|---|---|---|---|
| 7,744,882 | B2 | 6/2010 | Maihle et al. |
| 2012/0107234 | A1 | 5/2012 | Pedersen et al. |

FOREIGN PATENT DOCUMENTS

| WO | 91/08214 | 6/1991 |
|---|---|---|
| WO | 97/35885 | 10/1997 |
| WO | 00/78347 | 12/2000 |
| WO | 02/060470 | 8/2002 |
| WO | 03/013602 | 2/2003 |
| WO | 03/080835 | 10/2003 |
| WO | 2006/029275 | 3/2006 |
| WO | 2007/077028 | 7/2007 |
| WO | 2008/064884 | 6/2008 |
| WO | 2008/100624 | 8/2008 |
| WO | 2009/156179 | 12/2009 |
| WO | 2010/019952 | 2/2010 |
| WO | 2010/083470 | 7/2010 |
| WO | 2010/115552 | 10/2010 |
| WO | 2010/127181 | 12/2010 |
| WO | 2011/022727 | 2/2011 |
| WO | 2011/044311 | 4/2011 |
| WO | 2011/056124 | 5/2011 |
| WO | 2011/060206 | 5/2011 |
| WO | 2011/112953 | 9/2011 |
| WO | 2011/136911 | 11/2011 |
| WO | 2012/018404 | 2/2012 |
| WO | 2012/019024 | 2/2012 |
| WO | 2012/022814 | 2/2012 |
| WO | 2012/031198 | 3/2012 |
| WO | 2012/044612 | 4/2012 |
| WO | 2012/052230 | 4/2012 |
| WO | 2012/059224 | 5/2012 |
| WO | 2012/059858 | 5/2012 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
(International Preliminary Examination Report for PCT/EP2010/070062 Jun. 26, 2012).
(Written Opinion for PCT/EP2010/070062 Jun. 26, 2012).
Alimandi, M. et al., Oncogene 10:1813-1821 ( 1995).
Hellyer, N. J. et al., "Heregulin-dependent Activation of Phosphoinositide 3-Kinase and Akt via the ErbB2/ErbB3 Co-receptor" J Biol Chem 276:42153-42161 ( 2001).
Htun van der Horst, E. et al., "Anti-HER-3 MAbs inhibit HER-3-mediated signaling in breast cancer cell lines resistant to anti-HER-2 antibodies" Int J Cancer 115:519-527 ( 2005).
Kraus et al., "Demonstration of ligand-dependent signaling by the erbB-3 tyrosine kinase and its constitutive activation in human breast tumor cells" P Natl Acad Sci USA 90:2900-2904 ( 1993).
Kraus et al., "Isolation and characterization of ERBB3, a third member of the ERBB/epidermal growth factor receptor family: Evidence for overexpression in a subset of human mammary tumors" P Natl Acad Sci USA 86:9193-9197 (Dec. 1989).
Plowman et al., "Molecular cloning and expression of an additional epidermal growth factor receptor-related gene" P Natl Acad Sci USA 87:4905-4909 ( 1990).
Robinson et al., "Targeting ErbB2 and ErbB3 with a bispecific single-chain Fv enhances targeting selectivity and induces a therapeutic effect in vitro" Brit J Cancer 99:1415-1425 ( 2008).
Schaefer, K-L. et al., "Constitutive Activation of Neuregulin/ERBB3 Signaling Pathway in Clear Cell Sarcoma of Soft Tissue" Neoplasia 8:613-622 ( 2006).
Schoeberl, B. et al., "An ErbB3 Antibody, MM-121, Is Active in Cancers with Ligand-Dependent Activation" Cancer Res 70:2485-2494 (Mar. 2020).

(Continued)

*Primary Examiner* — Brad Duffy

(74) *Attorney, Agent, or Firm* — Traci H. Ropp

(57) ABSTRACT

The present invention relates to antibodies binding to human HER3 (anti-HER3 antibody), methods for their production, pharmaceutical compositions containing said antibodies, and uses thereof.

7 Claims, 6 Drawing Sheets

(56) References Cited

OTHER PUBLICATIONS

Sheng, Q. et al., "An Activated ErbB3/NRG1 Autocrine Loop Supports In Vivo Proliferation in Ovarian Cancer Cells" Cancer Cell 17:298-310 (Mar. 2010).

Singer, E. et al., "Identification of a Heregulin Binding site in HER3 Extracellular Domain" J Biol Chem 276:44266-44274 (2001).

Sliwkowski et al., "Coexpression of erbB2 and erbB3 Proteins Reconstitutes a High Affinity Receptor for Heregulin" J Biol Chem 269(20):14661-14665 (May 20, 1994).

Treder, M. et al., "309 Poster Fully Human anti-HER3 mAb U3-1287 (AMG 888) demonstrates unique in vitro and in vivo activities versus other HER family inhibitors in NSCLC models" Eur J Cancer Supp. 6(12) (Oct. 2008).

* cited by examiner

ANTI-HER3 ANTIBODIES AND USES THEREOF

The present invention relates to antibodies binding to human HER3 (anti-HER3 antibody), methods for their production, pharmaceutical compositions containing said antibodies, and uses thereof.

BACKGROUND OF THE INVENTION

Human HER3 (ErbB-3, ERBB3, c-erbB-3, c-erbB3, receptor tyrosine-protein kinase erbB-3, SEQ ID NO: 17) encodes a member of the epidermal growth factor receptor (EGFR) family of receptor tyrosine kinases which also includes HER1 (also known as EGFR), HER2, and HER4 (Kraus, M. H. et al, PNAS 86 (1989) 9193-9197; Plowman, G. D. et al, PNAS 87 (1990) 4905-4909; Kraus, M. H. et al, PNAS 90 (1993) 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound protein has HER3 a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski M. X., et al, J. Biol. Chem. 269 (1994) 14661-14665; Alimandi M, et al, Oncogene. 10 (1995) 1813-1821; Hellyer, N. J., J. Biol. Chem. 276 (2001) 42153-4261; Singer, E., J. Biol. Chem. 276 (2001) 44266-44274; Schaefer, K. L., Neoplasia 8 (2006) 613-622).

Amplification of this gene and/or overexpression of its protein have been reported in numerous cancers, including prostate, bladder, and breast tumors. Alternate transcriptional splice variants encoding different isoforms have been characterized. One isoform lacks the intermembrane region and is secreted outside the cell. This form acts to modulate the activity of the membrane-bound form. Additional splice variants have also been reported, but they have not been thoroughly characterized.

WO 97/35885 relates to HER3 antibodies. WO 2003/013602 relates to inhibitors of HER activity, including HER antibodies. WO 2007/077028 and WO 2008/100624 also relate to HER3 antibodies.

SUMMARY OF THE INVENTION

One aspect of the invention provides for an isolated antibody which binds to human HER3, wherein the heavy chain variable domain of the antibody comprises a CDR3H region of SEQ ID NO: 1, a CDR2H region of SEQ ID NO: 2, and a CDR1H region of SEQ ID NO:3, and the light chain variable domain of the antibody comprises a CDR3L region of SEQ ID NO: 4, a CDR2L region of SEQ ID NO:5, and a CDR1L region selected from SEQ ID NO:6 or SEQ ID NO:7.

Another aspect of the invention provides for an isolated antibody which binds to human HER3, wherein the antibody comprises a heavy chain variable domain VH of SEQ ID NO:8; and a light chain variable domain VL of SEQ ID NO:9, or SEQ ID NO:10, or SEQ ID NO:11.

Another aspect of the invention provides for an isolated antibody which binds to human HER3 where the antibody comprises a heavy chain variable domain comprising a CDR3H region of SEQ ID NO: 1, a CDR2H region of SEQ ID NO: 2, and a CDR1H region of SEQ ID NO:3, and a light chain variable domain comprising a CDR3L region of SEQ ID NO: 4, a CDR2L region of SEQ ID NO:5, and a CDR1L region of SEQ ID NO:6.

Another aspect of the invention provides for an isolated antibody which binds to human HER3 where the antibody comprises a heavy chain variable domain VH of SEQ ID NO:8; and the light chain variable domain VL of SEQ ID NO:9 or SEQ ID NO:11.

Another aspect of the invention provides for an isolated antibody which binds to human HER3 where the antibody comprises a heavy chain variable domain comprising a CDR3H region of SEQ ID NO: 1, a CDR2H region of SEQ ID NO: 2, and a CDR1H region of SEQ ID NO:3, and the light chain variable domain comprising a CDR3L region of SEQ ID NO: 4, a CDR2L region of SEQ ID NO:5, and a CDR1L region of SEQ ID NO:7.

Another aspect of the invention provides for an isolated antibody which binds to human HER3 where the antibody comprises a heavy chain variable domain VH of SEQ ID NO:8; and a light chain variable domain VL of SEQ ID NO:10.

Another aspect of the invention provides for an isolated antibody which binds to human HER3, where the antibody comprises a heavy chain variable domain VH having at least 95% sequence identity to SEQ ID NO:8 and a light chain variable domain VL having at least 95% sequence identity to SEQ ID NO:9, SEQ ID NO:10, or SEQ ID NO:11.

In one embodiment the antibody is a monoclonal antibody.

In one embodiment the antibody is humanized.

In one embodiment the antibody is characterized in that the antibody is of IgG1, or IgG4 subclass.

In one embodiment, the anti-HER antibody is glycosylated with a sugar chain at Asn297 whereby the amount of fucose within said sugar chain is 65% or lower.

Another aspect of the invention provides for a pharmaceutical composition comprising an antibody according to the invention and a pharmaceutical carrier.

Yet another aspect of the invention provides for a method for the treatment of a patient suffering from cancer comprising administering to the patient an antibody provided herein.

Another aspect of the invention provides for a nucleic acid encoding a heavy and a light chain of an anti-HER3 antibody provided herein. In one embodiment, the antibody comprises a heavy chain variable domain VH having at least 95% sequence identity to SEQ ID NO:8 and a light chain variable domain VL having at least 95% sequence identity to SEQ ID NO:9, SEQ ID NO:10, or SEQ ID NO:11. In one embodiment, the antibody comprises a variable domain VH of SEQ ID NO:8; and a light chain variable domain VL of SEQ ID NO:8, SEQ ID NO:10, or SEQ ID NO:11.

Yet another aspect of the invention provides for an expression vector comprising a nucleic acid for the expression of an anti-HER3 antibody provided herein in a prokaryotic or eukaryotic host cell. Another aspect of the invention provides for a prokaryotic or eukaryotic host cell comprising the expression vector. The invention further comprises a method for the production of a recombinant antibody which binds to HER3 described herein, wherein the method comprises culturing the host cell so that the antibody is produced. In one embodiment, the antibody is recovered from the host cell.

Surprisingly it was found that the antibodies according to the invention have highly valuable properties such as strong growth inhibition of HER3 expressing cancer cells, strong inhibition of HER3 mediated signal transduction (such as e.g HER3 phoshorylation and AKT phosphorylation) which is related to cancer cell proliferation, high binding affinity to HER3, or excellent pharmacokinetic properties (such as long half time, etc.).

DETAILED DESCRIPTION OF THE INVENTION

Figure 1A:
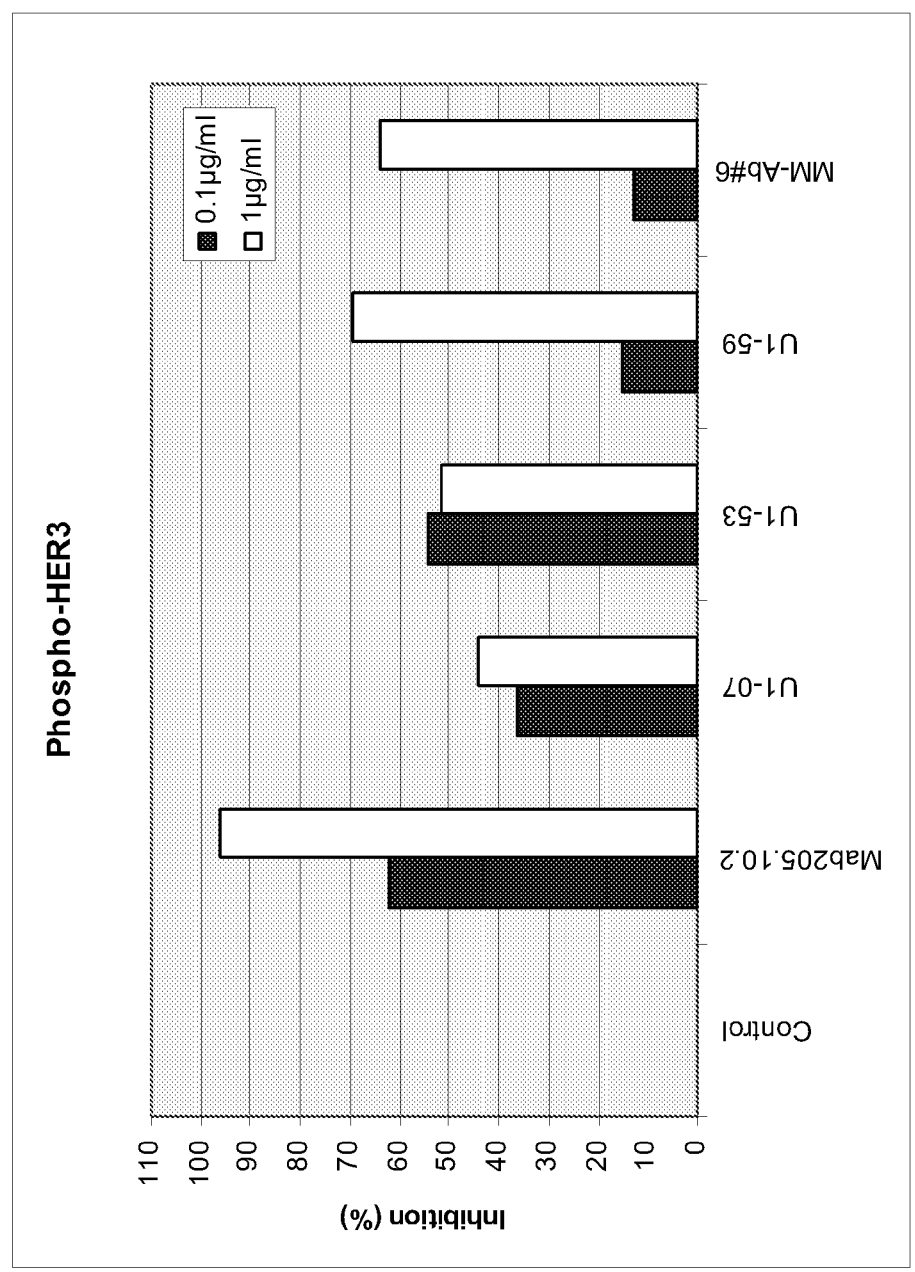
FIGS. 1A and B: Percent (%) inhibition of anti-HER3 antibodies on receptor phosphorylation in MCF7 cells in different concentrations FIG. 1C Percent (%) inhibition of anti-HER3 antibodies on receptor phosphorylation in Mel-Juso cells in different concentrations FIG. 2 Treatment with Mab 205 (10 mg/kg q7dx3, i.p.) resulted in tumor stasis of FaDu SCCHN transplanted xenografts FIG. 3 Treatment with Mab 205 (10 mg/kg q7d, i.p.) resulted in tumor stasis of MAXF449 breast cancer transplanted xenografts FIG. 4 Treatment with Mab 205 (25 mg/kg q7d, i.p.) resulted in tumor stasis of 7177 NSCLC transplanted xenografts

The invention comprises an antibody which binds to human HER3, characterized in that the heavy chain variable domain comprises a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6 or a CDR1L region of SEQ ID NO:7.

The invention further comprises an antibody according to the invention characterized in that the heavy chain variable domain VH is SEQ ID NO:8; and the light chain variable domain VL is SEQ ID NO:9, or the light chain variable domain VL is SEQ ID NO:10, or the light chain variable domain VL is SEQ ID NO:11; or a humanized version thereof.

In one embodiment the antibody according to the invention is characterized in comprising as the heavy chain variable domain a CDR3H region of SEQ ID NO: 1, a CDR2H region of SEQ ID NO: 2, and a CDR1H region of SEQ ID NO:3, and comprising as the light chain variable domain a CDR3L region of SEQ ID NO: 4, a CDR2L region of SEQ ID NO:5, and a CDR1L region of SEQ ID NO:6.

In one embodiment the antibody according to the invention is characterized in that the heavy chain variable domain VH is SEQ ID NO:8; and the light chain variable domain VL is SEQ ID NO:9 or the light chain variable domain VL is SEQ ID NO:11.

In one embodiment the antibody according to the invention is characterized in comprising a heavy chain variable domain comprising a CDR3H region of SEQ ID NO: 1, a CDR2H region of SEQ ID NO: 2, and a CDR1H region of SEQ ID NO:3, and a light chain variable domain comprising a CDR3L region of SEQ ID NO: 4, a CDR2L region of SEQ ID NO:5, and a CDR1L region of SEQ ID NO:7.

In one embodiment the antibody according to the invention is characterized in that the heavy chain variable domain VH is SEQ ID NO:8; and the light chain variable domain VL is SEQ ID NO:10.

In one embodiment the antibody the according to the invention is monoclonal. In one embodiment the antibody according to the invention is humanized or human.

In one embodiment the antibody according to the invention is of IgG1 or IgG4 subclass. In one embodiment the antibody according to the invention is a monoclonal humanized antibody of IgG1 subclass. In one embodiment the antibody according to the invention is characterized in that said antibody is glycosylated with a sugar chain at Asn297 whereby the amount of fucose within said sugar chain is 65% or lower.

The invention comprises the humanized antibodies Mab 205.10.1, Mab 205.10.2 and Mab 205.10.3 with their respective VH and VL or CDRs.

| Antibody | VH | VL |
|---|---|---|
| Mab 205.10.1 | SEQ ID NO: 8 | SEQ ID NO: 9 |
| Mab 205.10.2 | SEQ ID NO: 8 | SEQ ID NO: 10 |
| Mab 205.10.3 | SEQ ID NO: 8 | SEQ ID NO: 11 |

| Antibody | CDR3H | CDR2H | CDR1H | CDR3L | CDR2L | CDR1L |
|---|---|---|---|---|---|---|
| Mab 205.10.1 | SEQ ID NO: 1 | SEQ ID NO: 2 | SEQ ID NO: 3 | SEQ ID NO: 4 | SEQ ID NO: 5 | SEQ ID NO: 6 |
| Mab 205.10.2 | SEQ ID NO: 1 | SEQ ID NO: 2 | SEQ ID NO: 3 | SEQ ID NO: 4 | SEQ ID NO: 5 | SEQ ID NO: 7 |
| Mab 205.10.3 | SEQ ID NO: 1 | SEQ ID NO: 2 | SEQ ID NO: 3 | SEQ ID NO: 4 | SEQ ID NO: 5 | SEQ ID NO: 6 |

In one embodiment such antibodies comprise constant regions of human origin e.g. SEQ ID NO:12-16. In one embodiment, the antibody comprises one or both of SEQ ID NO:12 and 13.

The term "antibody" encompasses the various forms of antibody structures including, but not being limited to, whole antibodies and antibody fragments. The antibody according to the invention is preferably a human antibody, humanized antibody, chimeric antibody, or further genetically engineered antibody as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to HER3, namely being able to assemble together with a $V_H$ domain to a functional antigen binding site and thereby providing the properties of an antibody according to the invention.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" or "humanized version of an antibody" refers to antibodies in which the framework or "complementarity determining regions" (CDR) have been modified to comprise the CDR of an immunoglobulin of different specificity as compared to that of the parent immunoglobulin. In a preferred embodiment, the CDRs of the VH and VL are grafted into the framework region of human antibody to prepare the "humanized antibody." See e.g. Riechmann, L., et al., Nature 332 (1988) 323-327; and Neuberger, M. S., et al., Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix 1P A.1P.1-A.1P.37 and are accessible via IMGT, the international ImMunoGeneTics information System® (http://imgt-.cines.fr) or via http://vbase.mrc-cpe.cam.ac.uk. Optionally the framework region can be modified by further mutations. Particularly preferred CDRs correspond to those representing sequences recognizing the antigens noted above for chimeric antibodies. Preferably such humanized version is chimerized with a human constant region (see e.g. Sequences SEQ ID NO:12-16). The term "humanized antibody" as used herein also comprises such antibodies which are modified in the constant region to generate the properties according to the invention, especially in regard to Clq binding and/or FcR binding, e.g. by "class switching" i.e. change or mutation of Fc parts (e.g. from IgG1 to IgG4 and/or IgG1/IgG4 mutation.)

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M. D., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. L., p. 77 (1985); and Boerner, P., et al., J. Immunol. 147 (1991) 86-95). As already mentioned for and humanized antibodies according to the invention the term "human antibody" as used herein also comprises such antibodies which are modified in the constant region to generate the properties according to the invention, especially in regard to Clq binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, the terms "binding to human HER3", "binds to human HER3", "specifically binding to human HER3", or "anti-HER3 antibody" are interchangeable and refer to an antibody which specifically binds to the human HER3 antigen with a binding affinity of KD-value of $1.0 \times 10^{-8}$ mol/l or lower at 25° C., in one embodiment of a KD-value of $1.0 \times 10^{-9}$ mol/l or lower at 25° C. The binding affinity is determined with a standard binding assay at 25° C., such as surface plasmon resonance technique (BIAcore®, GE-Healthcare Uppsala, Sweden). A method for determining the KD-value of the binding affinity is described in Example 2b). Thus an "antibody binding to human HER3" or an "antibody which binds to human HER3" as used herein refers to an antibody which specifically binds to the human HER3 antigen with a binding affinity of KD $1.0 \times 10^{-8}$ mol/l or lower (preferably $1.0 \times 10^{-8}$ mol/l $-1.0 \times 10^{-12}$ mol/l) at 25° C.

Human HER3 (ErbB-3, ERBB3, c-erbB-3, c-erbB3, receptor tyrosine-protein kinase erbB-3, SEQ ID NO: 17) encodes a member of the epidermal growth factor receptor (EGFR) family of receptor tyrosine kinases which also includes HER1 (also known as EGFR), HER2, and HER4 (Kraus, M. H. et al, PNAS 86 (1989), 9193-9197; Plowman, G. D. et al, PNAS 87 (1990), 4905-4909; Kraus, M. H. et al, PNAS 90 (1993), 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound protein has HER3 a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski, M. X., et al, J. Biol. Chem. 269 (1994) 14661-14665; Alimandi, M., et al, Oncogene 10 (1995) 1813-1821; Hellyer, N. J., J. Biol. Chem. 276 (2001) 42153-421561;

Singer, E., J. Biol. Chem. 276 (2001) 44266-44274; Schaefer, K. L., Neoplasia 8 (2006) 613-622).

HER3 antibodies Mab205.10.1, Mab205.10.2, and Mab205.10.3 showed a competitive binding with the ligand Heregulin (HRG) to HER3.

Amplification of this gene and/or overexpression of its protein have been reported in numerous cancers, including prostate, bladder, and breast tumors. Alternate transcriptional splice variants encoding different isoforms have been characterized. One isoform lacks the intermembrane region and is secreted outside the cell. This form acts to modulate the activity of the membrane-bound form. Additional splice variants have also been reported, but they have not been thoroughly characterized.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The "variable domain of an antibody according to the invention" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". The term "antigen-binding portion" of an antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The term "CDRH1" denotes the CDR1 region of the heavy chain variable region calculated according to Kabat. CDRH2, CDRH3, CDRL1, CDRL2 and CDRL3 mean the respective regions from the heavy (H) or light (L) chain. The extent of CDR and framework regions (FRs) is determined by comparison to a compiled database of amino acid sequences in which those regions have been defined according to variability among the sequences according to Kabat et al, Sequences of Proteins of Immunological Interest, 5th Ed. Public Health Service, National Institutes of Health, Bethesda, Md. (1991).

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, Clq binding and Fc receptor binding. The term "complement-dependent cytotoxicity (CDC)" denotes a process initiated by binding of complement factor Clq to the Fc part of most IgG antibody subclasses. Binding of Clq to an antibody is caused by defined protein-protein interactions at the so called binding site. Such binding sites are known in the state of the art and described e.g. by Boackle, R. J., et al., Nature 282 (1979) 742-743, Lukas, T. J., et al., J. Immunol. 127 (1981) 2555-2560, Brunhouse, R., and Cebra, J. J., Mol. Immunol. 16 (1979) 907-917, Burton, D. R., et al., Nature 288 (1980) 338-344, Thommesen, J. E., et al., Mol. Immunol. 37 (2000) 995-1004, Idusogie, E. E., et al., J. Immunol. 164 (2000) 4178-4184, Hezareh, M., et al., J. Virology 75 (2001) 12161-12168, Morgan, A., et al., Immunology 86 (1995) 319-324, EP 0 307 434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and Clq and C3 binding, whereas IgG4 do not activate the complement system and do not bind Clq and C3.

In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, e.g. a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). Preferred are the human heavy chain constant regions of SEQ ID NO: 13 (human IgG1 subclass), SEQ ID NO: 14 (human IgG1 subclass with mutations L234A and L235A).

In one embodiment the antibody according to the invention is of human IgG1 subclass or of human IgG3 subclass. In one embodiment the antibody according to the invention is of human IgG1 subclass.

In one embodiment the antibody according to the invention is characterized in that the constant chains are of human origin. Such constant chains are well known in the state of the art and e.g. described by Kabat, E. A., (see e.g. Johnson, G. and Wu, T. T., Nucleic Acids Res. 28 (2000) 214-218). For example, a useful human heavy chain constant region comprises an amino acid sequence of SEQ ID NO: 13. For example, a useful human light chain constant region comprises an amino acid sequence of a kappa-light chain constant region of SEQ ID NO: 12.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The terms "nucleic acid" or "nucleic acid molecule", as used herein, are intended to include DNA molecules and RNA molecules. A nucleic acid molecule may be single-stranded or double-stranded, but preferably is double-stranded DNA. A nucleic acid is "operably linked" when it is placed into a functional relationship with another nucleic acid. For example, DNA for a presequence or secretory leader is operable linked to DNA for a polypeptide if it is expressed as a preprotein that participates in the secretion of the polypeptide; a promoter or enhancer is operable linked to a coding sequence if it affects the transcription of the sequence; or a ribosome binding site is operable linked to a coding sequence if it is positioned so as to facilitate translation. Generally, "operable linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice. As used herein, the expressions "cell", "cell line", and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The antibody according to the invention is preferably characterized in that the constant chains are of human origin. Such constant chains are well known in the state of the art and described, e.g., by Kabat et al., Sequences of Proteins of Immunological Interest, 5th ed., Public Health Service, National Institutes of Health, Bethesda, Md. (1991). For example, a useful human light chain constant region comprises an amino acid sequence of a kappa-light chain constant region of SEQ ID NO:12. For example, useful human heavy chain constant region comprises SEQ ID NO:13 to 16.

A further embodiment of the invention is a nucleic acid encoding a heavy and a light chain of an antibody according to the invention.

The antibodies according to the invention include, in addition, such antibodies having "conservative sequence modifications" (variant antibodies), nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, a predicted nonessential amino acid residue in a human anti-HER3 antibody can be preferably replaced with another amino acid residue from the same side chain family. A "variant" anti-HER3 antibody, refers therefore herein to a molecule which differs in amino acid sequence from a "parent" anti-HER3 antibody amino acid sequence by up to ten, preferably from about two to about five, additions, deletions and/or substitutions in one or more variable region of the parent antibody. Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

In another aspect, an anti-HER3 antibody according to the invention comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:8. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti HER3 antibody comprising that sequence retains the ability to bind to HER3. In certain embodiments, a total of 1 to 10 amino acids have been substituted, inserted and/or deleted in SEQ ID NO:8. In certain embodiments, substitutions, insertions, or deletions occur in regions outside the CDRs (i.e., in the FRs). Optionally, the anti-HER3 antibody comprises the VH sequence in SEQ ID NO:8, including post-translational modifications of that sequence. In a particular embodiment, the VH comprises one, two or three CDRs selected from: (a) CDR1H comprising the amino acid sequence of SEQ ID NO:3, (b) CDR2H comprising the amino acid sequence of SEQ ID NO:2, and (c) CDR3H comprising the amino acid sequence of SEQ ID NO:1.

In another aspect, an anti-HER3 antibody according to the invention comprises a light chain variable domain (VL) having at least 90%, 91%, 92%, 93%, 94%, 95%, 96%, 97%, 98%, 99%, or 100% sequence identity to the amino acid sequence of SEQ ID NO:9, SEQ ID NO:10, or SEQ ID NO:11. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HER antibody comprising that sequence retains the ability to bind to HER. In certain embodiments, a total of 1 to 10 amino acids have been substituted, inserted and/or deleted in SEQ ID NO:9, SEQ ID NO:10, or SEQ ID NO:11. In certain embodiments, the substitutions, insertions, or deletions occur in regions outside the CDRs (i.e., in the FRs). Optionally, the anti-HER3 antibody comprises the VL sequence in SEQ ID NO:9, SEQ ID NO:10, or SEQ ID NO:11, including post-translational modifications of that sequence. In a particular embodiment, the VL comprises one, two or three CDRs selected from (a) CDR1L comprising the amino acid sequence of SEQ ID NO:6, or SEQ ID NO:7; (b) CDR2L comprising the amino acid sequence of SEQ ID NO:5; and (c) CDR3L comprising the amino acid sequence of SEQ ID NO:4.

In another aspect, an anti-HER3 antibody is provided, wherein the antibody comprises a VH as in any of the embodiments provided above, and a VL as in any of the embodiments provided above. In one embodiment, the antibody comprises the VH and VL sequences in SEQ ID NO:8 and SEQ ID NO:10, respectively, including post-translational modifications of those sequences; and having one or more of the following properties (determined in assays as described in Example 3 and 2):

the anti-HER3 antibody inhibits the HER3 phosphorylation in tumor cells such as MCF7 cells, FaDu cells or MeI-Juso cell (in one embodiment the anti-HER3 antibody shows an inhibition of the HER3 phosphorylation in MCF7 cells of at least 80% (in one embodiment at least 90%) at a concentration of 1.0 ng/ml; in one embodiment the anti-HER3 antibody shows an inhibition of the HER3 phosphorylation in FaDu cells of at least 80% (in one embodiment at least 90%) at a concentration of 0.1 ng/ml; in one embodiment the anti-HER3 antibody shows an inhibition of the HER3 phosphorylation in MeI-Juso cells of at least 60% (in one embodiment at least 70%) at a concentration of 0.1 µg/ml)

the anti-HER3 antibody inhibits the AKT phosphorylation in tumor cells such as MeI-Juso cell (in one embodiment the anti-HER3 antibody inhibits the AKT phosphorylation in MeI-Juso cells with an IC50 value of less than 0.50 µg/ml, in one embodiment with IC50 value of less than 0.35 µg/ml)

the anti-HER3 antibody inhibits the proliferation of tumor cells such as MDA-MB-175 cells (in one embodiment the anti-HER3 antibody inhibits the proliferation of MDA-MB-175 cells with an IC50 value of less than 10 µg/ml)

the anti-HER3 antibody binds to HER3 with a KD value of less than $5.0 \times 10^{-9}$ M, in one embodiment with a KD value of less than $3.0 \times 10^{-9}$ M.

In another aspect, an anti-HER3 antibody according to the inventions comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:8 and comprises a light chain variable domain (VL) having at least 90%, 91%, 92%, 93%, 94%, 95%, 96%, 97%, 98%, 99%, or 100% sequence identity to the amino acid sequence of SEQ ID NO:9, SEQ ID NO:10, or SEQ ID NO:11; and has one or more of the following properties (determined in assays as described in Example 3 and 2):

the anti-HER3 antibody inhibits the HER3 phosphorylation in tumor cells such as MCF7 cells, FaDu cells or MeI-Juso cell (in one embodiment the anti-HER3 antibody shows an inhibition of the HER3 phosphorylation in MCF7 cells of at least 80% (in one embodiment at least 90%) at a concentration of 1.0 µg/ml; in one embodiment the anti-HER3 antibody shows an inhibition of the HER3 phosphorylation in FaDu cells of at least 80% (in one embodiment at least 90%) at a concentration of 0.1 µg/ml; in on embodiment the anti-HER3 antibody shows an inhibition of the HER3 phosphorylation in MeI-Juso cells of at least 60% (in one embodiment at least 70%) at a concentration of 0.1 µg/ml)

the anti-HER3 antibody inhibits the AKT phosphorylation in tumor cells such as MeI-Juso cell (in one embodiment the anti-HER3 antibody inhibits the AKT phosphorylation in MeI-Juso cells with an IC50 value of less than 0.50 µg/ml, in one embodiment with IC50 value of at least 0.35 µg/ml)

the anti-HER3 antibody inhibits the proliferation of tumor cells such as MDA-MB-175 cells (in on embodiment the anti-HER3 antibody inhibits the proliferation of MDA-MB-175 cells with an IC50 value of less than 10 µg/ml)

the anti-HER3 antibody binds to HER3 with a KD value of less than $5.0 \times 10^{-9}$ M, in one embodiment with a KD value of less than $3.0 \times 10^{-9}$ M.

Identity or homology with respect to the sequence is defined herein as the percentage of amino acid residues in the candidate sequence that are identical with the parent sequence, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind the variable domain of human HER3 and preferably has properties, which are superior to those of the parent antibody. For example, the variant may have reduced side effects during treatment.

An exemplary "parent" antibody comprises the CDR regions of antibody Mab 205.10.2 and is preferably used for the preparation of the variant. Preferably, the parent antibody has a human framework region and, if present, has human antibody constant domains. For example, the parent antibody may be a humanized or a human antibody.

The term "antibody-dependent cellular cytotoxicity (ADCC)" refers to lysis of human target cells by an antibody according to the invention in the presence of effector cells. ADCC is measured preferably by the treatment of a preparation of HER3 expressing cells with an antibody according to the invention in the presence of effector cells such as freshly isolated PBMC or purified effector cells from buffy coats, like monocytes or natural killer (NK) cells or a permanently growing NK cell line.

Cell-mediated effector functions like ADCC of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies via glycoengineering are reported e.g. in WO 2005/044859, WO 2004/065540, WO2007/031875, Umana, P., et al., Nature Biotechnol. 17 (1999) 176-180, WO 99/154342, WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835 and WO 2000/061739 or e.g. in Niwa, R., et al., J. Immunol. Methods 306 (2005) 151-160; Shinkawa, T., et al, J Biol Chem, 278 (2003) 3466-3473; WO 03/055993 and US 2005/0249722.

In one embodiment of the invention, the antibody according to the invention is afucosylated which means the antibody is glycosylated (if it comprises an Fc part of IgG1 or IgG3 subclass) with a sugar chain at Asn297 whereby the amount of fucose within said sugar chain is 80% or lower (Numbering according to Kabat), e.g. between 80% and 1%. In another embodiment is the amount of fucose within said sugar chain is 65% or lower, in one embodiment between 5% and 65%, and in one embodiment the amount of fucose within said sugar chain is 0%. Such antibodies are referred to in the following as "afucosylated antibodies" or "non-fucosylated antibodies". Such afucosylated antibodies show enhanced ADCC whereas other antibody properties remain substantially unaffected.

In a further embodiment the amount of N-glycolyl-neuraminic acid (NGNA) is 1% or less and/or the amount of N-terminal alpha-1,3-galactose is 1% or less within said sugar chain. The sugar chain show preferably the characteristics of N-linked glycans attached to Asn297 of an antibody recombinantly expressed in a CHO cell.

"Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300.

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolyl-neuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E., A., et al., Sequences of Proteins of Immunological Interest, 5th Ed. Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527. These structures are designated as G0, G1 (α-1,6- or α-1,3-), or G2 glycan residues, depending from the amount of terminal Gal residues (Raju, T. S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry (e.g. in LC/MS system) and calculated as average value (see e.g WO 2008/077546). The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis). Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880. The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including, column chromatography and others well known in the art (see Ausubel, F., et al., ed. Current Protocols in Molecular Biology, Greene Publishing and Wiley Interscience, New York (1987)). Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199. Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells. Antibodies obtainable from said cell lines are preferred embodiments of the invention. Afocusylated antibodies are preferably prepared via glycoengineering as described above.

Amino acid sequence variants of anti-HER3 antibody are prepared by introducing appropriate nucleotide changes into the antibody encoding DNA, or by peptide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability, or facilitate the purification. Any cysteine residue not involved in maintaining the proper conformation of the anti-HER3, antibody may also be substituted, generally with serine, to improve the oxidative stability of the molecule and to prevent aberrant crosslinking. Conversely, cysteine bond(s) may be added to the antibody to improve its stability (particularly where the antibody is an antibody fragment such as an Fv fragment). Another type of amino acid variant of the antibody alters the original glycosylation pattern of the antibody. By "altering" is meant removing one or more carbohydrate moieties found in the antibody and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-HER3 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-HER3 antibody.

Another type of covalent modification of the antibody comprises linking the antibody to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; 4,179,337.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

Furthermore the anti-HER3 antibodies according to the invention are useful for the treatment of cancer.

Therefore one aspect of the invention is said pharmaceutical composition for the treatment of cancer.

Another aspect of the invention is an antibody according to the invention for the treatment of cancer.

Another aspect of the invention is the use of an antibody according to the invention for the manufacture of a medicament for the treatment of cancer.

Another aspect of the invention is a method of treatment of a patient suffering from cancer by administering an antibody according to the invention to said patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, lung cancer, cancer of the head or neck, or pancreatic cancer, preferably lung cancer, cancer of the head or neck, or pancreatic cancer. Preferably such cancers are further characterized by HER3 expression or overexpression, more preferably by HER3 overexpression.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The following examples, sequence listing and figures are provided to aid the understanding of the present invention, the true scope of which is set forth in the appended claims. It is understood that modifications can be made in the procedures set forth without departing from the spirit of the invention.

All references cited herein, including patent applications and publications, are incorporated by reference in their entirety.

DESCRIPTION OF THE SEQUENCE LISTING

SEQ ID NO: 1 heavy chain CDR3H, Mab 205.10
SEQ ID NO: 2 heavy chain CDR2H, Mab 205.10
SEQ ID NO: 3 heavy chain CDR1H, Mab 205.10
SEQ ID NO: 4 light chain CDR3L, Mab 205.10
SEQ ID NO: 5 light chain CDR2L, Mab 205.10
SEQ ID NO: 6 light chain CDR1L (variant 1), Mab 205.10
SEQ ID NO: 7 light chain CDR1L (variant 2), Mab 205.10
SEQ ID NO: 8 heavy chain variable domain VH, Mab 205.10
SEQ ID NO: 9 light chain variable domain VL, Mab 205.10.1
SEQ ID NO: 10 light chain variable domain VL, Mab 205.10.2
SEQ ID NO: 11 light chain variable domain VL, Mab 205.10.3
SEQ ID NO: 12 human kappa light chain constant region
SEQ ID NO: 13 human heavy chain constant region derived from IgG1
SEQ ID NO: 14 human heavy chain constant region derived from IgG1 mutated on L234A and L235A
SEQ ID NO: 15 human heavy chain constant region derived from IgG4
SEQ ID NO: 16 human heavy chain constant region derived from IgG4 mutated on S228P
SEQ ID NO: 17 human HER3

EXAMPLES

Example 1

Immunisation

NMRI mice were immunized with hHER3-ECD (inhouse) and boosted with hu-HER3-ECD. The immune response was monitored by testing serum samples against the HER1/2/3-ECD-ELISA. Spleen cells from mice with sufficient titers of anti-HER3 immunoglobulin were frozen for later immortalization by fusion with mouse myeloma cell line P3X63 Ag8.653. One fusion was done and hybridoma supernatants screened by HER1/2/-ECD-ELISA showing no cross-reacivity, but binding to HER3-ECD and anti-HER3 selective hybridomas were selected. The relevant hybridomas were cloned by single cell FACS sorting. Single cell clones from different hybridomas were cultured in vitro to produce antibody in tissue culture medium for characterization. Antibodies were selected by determining their ability to inhibit HER3 phosphorylation, AKT phosphorylation and tumor cell proliferation of MDA-MB-175 cells (see Examples below). From the obtained antibodies, one was further humanized to give the following antibodies Mab 205.10.1, Mab 205.10.2 and Mab 205.10.3 with their respective VH and VL or CDRs.

| Antibody | VH | VL |
| --- | --- | --- |
| Mab 205.10.1 | SEQ ID NO: 8 | SEQ ID NO: 9 |
| Mab 205.10.2 | SEQ ID NO: 8 | SEQ ID NO: 10 |
| Mab 205.10.3 | SEQ ID NO: 8 | SEQ ID NO: 11 |

| Antibody | CDR3H | CDR2H | CDR1H | CDR3L | CDR2L | CDR1L |
| --- | --- | --- | --- | --- | --- | --- |
| Mab 205.10.1 | SEQ ID NO: 1 | SEQ ID NO: 2 | SEQ ID NO: 3 | SEQ ID NO: 4 | SEQ ID NO: 5 | SEQ ID NO: 6 |
| Mab 205.10.2 | SEQ ID NO: 1 | SEQ ID NO: 2 | SEQ ID NO: 3 | SEQ ID NO: 4 | SEQ ID NO: 5 | SEQ ID NO: 7 |
| Mab 205.10.3 | SEQ ID NO: 1 | SEQ ID NO: 2 | SEQ ID NO: 3 | SEQ ID NO: 4 | SEQ ID NO: 5 | SEQ ID NO: 6 |

In one embodiment such antibodies were prepared using constant regions of human origin e.g. SEQ ID NO:12-13.

Example 2

Binding Assays a) Antigene Specific ELISA for Binding to Human HER3 ECD

Soluble human HER3 extracellular domain fused to Streptavidin Binding Protein (SBP) was captured on a streptavidin plate. To define optimal binding of the antibody to SPB-CDCP1, 384-well polystyrene plates (NUNC, streptavidin-coated) delivered by MicroCoat, Bernried, Germany (ID-No. 1734776-001) were coated with pure and stepwise diluted HEK293 supernatant (in BSA/IMDM buffer: 100 mg/ml BSA Fraction V, Roche 10735078001, dissolved in Iscove's Modified Dulbeccos Medium). Using a calibration curve of chimeric 205 antibodies, the optimal dilution factor of the HEK293 supernatant in relation to the streptavidin binding capacity of the microtiter plate was identified. For the standard coating, SBP-HER3 containing HEK293 supernatant was diluted (between 1:15 and 1:40) and incubated overnight at 2-80 C (25 μl per well). Intensive washing of the microtiter plate was necessary to remove remaining unbound SBP-HER3.

Antibodies were tested either undiluted or using a 12-step-dilution. 12.5 μl per well of each sample was incubated for 90 min at room temperature. After intensive washing using PBS-T (0.1% Tween 20 in PBS) 25 μl goat anti-human IgG antibodies coupled with HRP (Jackson ImmunoResearch, Code No: 109-036-098, dilution 1:10000) for human antibodies were added and incubated for 1 hour. After intensive washing the binding of the antibodies was detected with ABTS tablets (Roche Diagnostics GmbH, Cat. No.: 1112422). Absorbance at 405 nm/492 nm was measured using a standard photometer.

The table shows the relative binding ratios of the different antibodies.

| antibody | hu_HER3-ECD-ELISA c (μg/ml) | IgG-ELISA c (μg/ml) | activity (ratio binding to hu_HER3-ECD/IgG) |
|---|---|---|---|
| Mab 205.10.1 | 583.,1 | 785.,0 | 0.74 |
| Mab 205.10.2 | 396.,4 | 508.,0 | 0.,78 |
| Mab 205.10.3 | 505.4 | 608.4 | 0.83 | b) Characterization of the Binding of Anti-HER3 Antibodies to a Extracellular-Domain-(ECD) Fragment of Human HER3 by Biacore Analyses:

For affinity measurements, 30 μg/ml of anti Fcγ antibodies (from goat, Jackson Immuno Research) were coupled to the surface of a CM-5 sensor chip by standard amine-coupling and blocking chemistry on a SPR instrument (Biacore T100). After conjugation, anti-HER3 antibodies were injected at 25° C. at a flow rate of 5 μL/min, followed by a dilution series (0 nM to 1000 nM) of human HER3 ECD at 30 μL/min. As running buffer for the binding experiment PBS/0.1% BSA was used. The chip was then regenerated with a 60 s pulse of 10 mM glycine-HCl, pH 2.0 solution.

Calculation of thermodynamic parameters ($K_D$, binding constant to HER3) were calculated using a Langmuir 1:1 binding model.

| Antibody | Binding Affinity KD [M] |
|---|---|
| Mab 205.10.1 | $2.0 \times 10^{-9}$ |
| Mab 205.10.2 | $1.1 \times 10^{-9}$ |
| Mab 205.10.3 | $2.0 \times 10^{-9}$ |

In a competitive binding assay (Biacore) Mab205.10.1, Mab205.10.2, and Mab205.10.3 all showed binding to the same epitope. The anti-HER3-antibodies U1-7, U-53 and U1-59 described in WO 2007/077028 and Ab#6 described in WO 2008/100624 were investigated in such assay and revealed to bind to different epitopes than antibodies Mab205.10.1. Mab205.10.2, and Mab205.10.3.

Example 3 a) Inhibition of HER3 Phosphorylation in MCF7, FaDu and MeI-Juso Cells

Assays were performed in MCF7 and FaDu cells according to the following protocol: Poly-D-Lysine coated 6-well plates were seeded with 500,000 cells/well in RPMI1640 medium with 10% FCS and incubated for 24 h. Medium was removed by aspirating and the plates were incubated overnight with 5000/well RPMI 1640 with 0.5% FCS. Antibodies were added in 500 μl RPMI 1640 with 0.5% FCS and the plates were incubated for 1 h. HRG-1b (final concentration 500 ng/ml) was added for 10 min. Cells were lysed by removing medium and adding 80 μl ice cold Triton-X-100 cell lysis buffer and incubating for 5 minutes on ice. After transferring the lysate into 1.5 ml reaction tube and centrifugation at 14000 rpm for 15 min at 4° C., the supernatant was transferred into fresh reaction tubes.

Samples containing equal amounts of protein in SDS loading buffer were separated on SDS PAGE and blotted by using a semi-dry Western Blot to nitrocellulose membranes. Membranes were blocked by 1xNET-buffer+0.25% gelatine for 1 h hour and pHER3 was detected by the antibody aPhospho-HER3/ErbB3 (Tyr1289)(21D3), Cell Signaling, #4791, and HER3 by the antibody aErbB3 (C-17), Santa Cruz, #sc-285 respectively. After washing and detection of the signals by an POD coupled secondary antibody, bands were densometricaly scanned. The anti-HER3 antibodies Mab205.10.1, Mab205.10.2, and Mab205.10.3 and also anti-HER3 antibodies U1-7, U-53 and U1-59 described in WO 2007/077028 and Ab#6 described in WO 2008/100624 were investigated. Percent (%) inhibition of anti-HER3 antibodies on receptor phosphorylation in MCF7 cells is shown below and in FIG. 1A.

| | % Inhibition of HER3 phosphorylation in MCF7 cells | |
|---|---|---|
| Antibody | pHER3 % inhibition [0.1 μg/ml] | pHER3 % inhibition [1.0 μg/ml] |
| control | 0 | 0 |
| Mab205.10.2 | 62 | 96 |
| U1-7 | 36 | 44 |
| U1-53 | 54 | 51 |
| U1-59 | 15 | 70 |
| Ab#6 | 13 | 64 |

Figure 1B:
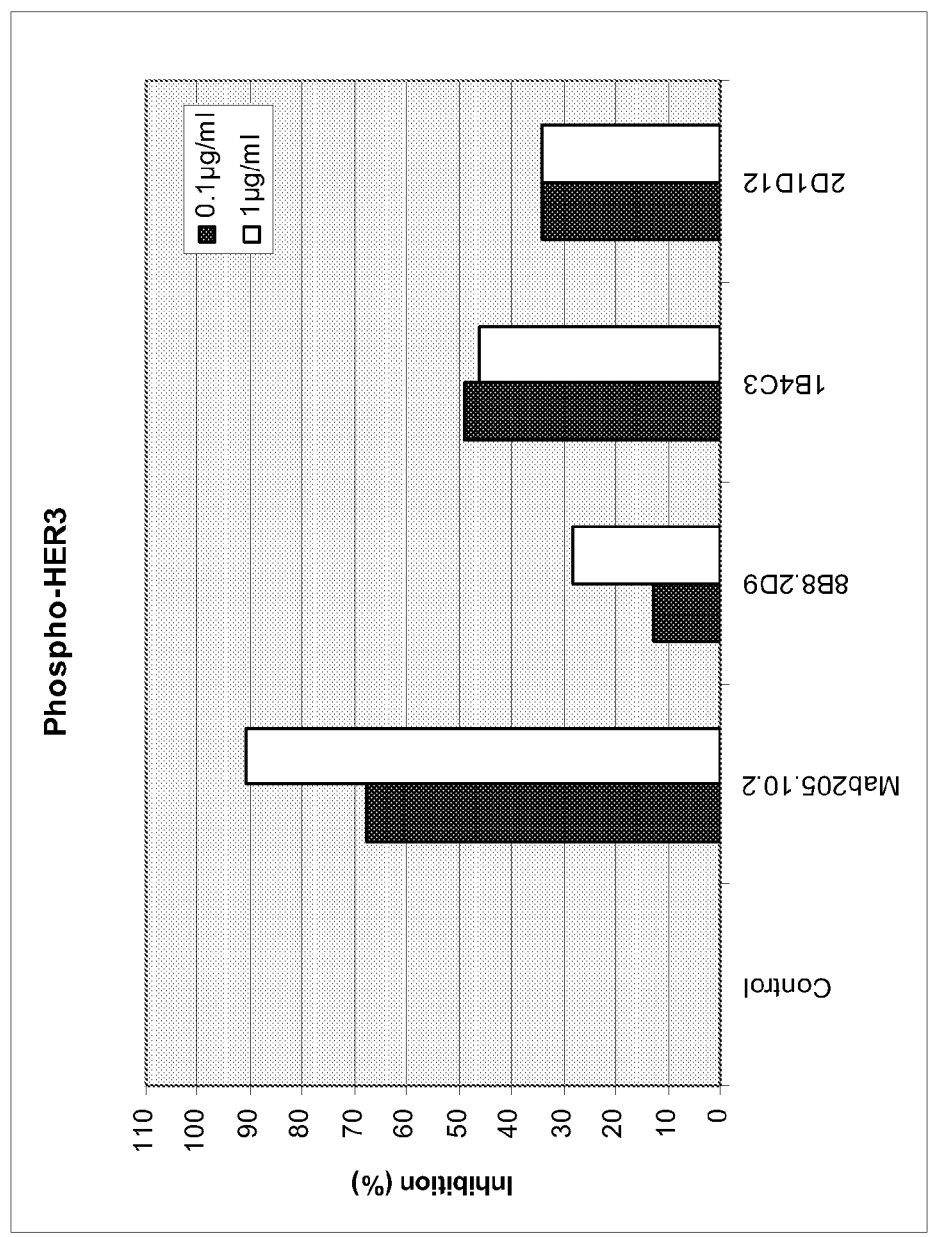

In a further experiment the anti-HER3 antibody Mab205.10.2, and also the anti-HER3-antibodies 8B8.2D9 described in WO 97/35885, and 1B4C3 and 2D1D12 described in WO 2003/013602 were investigated. Percent (%) inhibition of anti-HER3 antibodies on receptor phosphorylation in MCF7 cells is shown below and in FIG. 1B.

| | % Inhibition of HER3 phosphorylation in MCF7 cells | |
|---|---|---|
| Antibody | pHER3 % inhibition [0.1 μg/ml] | pHER3 % inhibition [1.0 μg/ml] |
| control | 0 | 0 |
| Mab205.10.2 | 68 | 91 |
| 8B8.2D9 | 13 | 28 |
| 1B4C3 | 49 | 46 |
| 2D1D12 | 34 | 34 |

Percent (%) inhibition of anti-HER3 antibodies on receptor phosphorylation in FaDu cells is shown below.

% Inhibition of HER3 phosphorylation in FaDu cells

| Antibody | pHER3 % Inhibition [0.03 μg/ml] | pHER3 % Inhibition [0.10 μg/ml] | pHER3 % Inhibition [0.30 μg/ml] |
|---|---|---|---|
| Control | 0 | 0 | 0 |
| Mab205.10.2 | 88 | 93 | 97 |
| U1-59 | 31 | 25 | 90 |

Figure 1C:
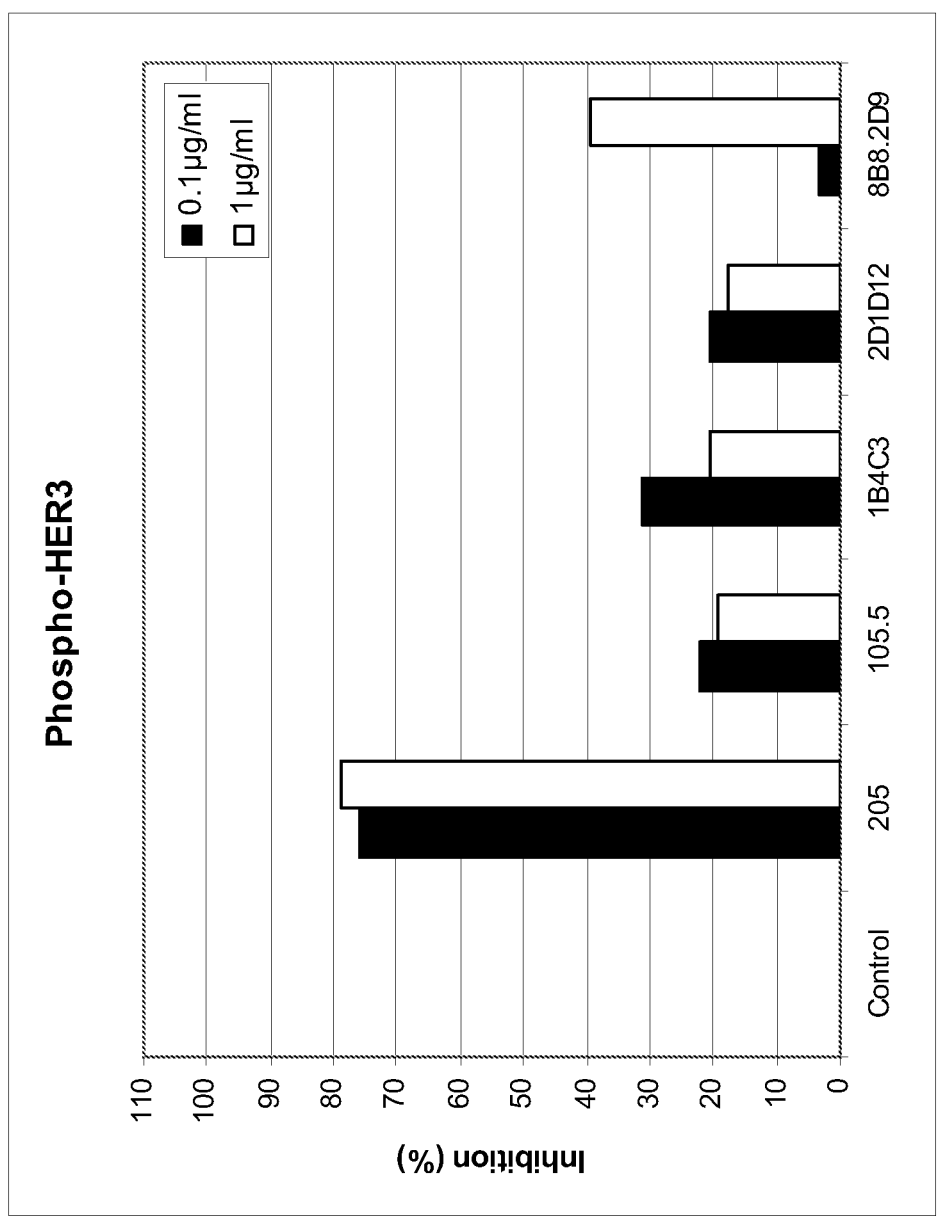

In a further experiment, the anti-HER3 antibody Mab205.10.2, and also the anti-HER3-antibodies 8B8.2D9 described in WO 97/35885, and 1B4C3 and 2D1D12 described in WO 2003/013602, and 105.5 from (Millipore, Cat. no. 05-47, named α-HER$^{ECD}$ in WO 2003/013602) were investigated in MeI-Juso cells. Assays in MeI-Juso cells were performed according to the aforementioned protocol for MCF7 and FaDu cells. Cell numbers and media volumes were adapted to 12-well plates Percent (%) inhibition of anti-HER3 antibodies on receptor phosphorylation in MeI-Juso cells is shown below and in FIG. 1C.

% Inhibition of HER3 phosphorylation in Mel-Juso cells

| Antibody | pHER3 % inhibition [0.1 μg/ml] | pHER3 % inhibition [1.0 μg/ml] |
|---|---|---|
| control | 0 | 0 |
| Mab205.10.2 | 75.9 | 78.8 |
| 105.5 (α-HER$^{ECD}$) | 22.2 | 19.5 |
| 8B8.2D9 | 31.3 | 20.3 |
| 1B4C3 | 20.7 | 17.5 |
| 2D1D12 | 3.4 | 39.3 | b) AKT Phosphorylation (ELISA)

Assays were performed in MCF7 cells according to the following protocol: MCF7 cells were seeded at 30000 cells/well into Poly-D-Lysine coated 96-well plate in RPMI1640 medium with 10% FCS and incubated for 24 h. Medium was removed by tapping on a clean paper towel and washing carefully with 200 μl serum-free medium. The cells were incubated overnight with 100 μl/well RPMI 1640 with 0.5% FCS. Medium was removed as described above. Antibodies in 100 μl RPMI 1640 with 0.5% FCS were added and the mixture incubated for 1.5 h. HRG-1b (final concentration 5 ng/ml) was added for 10 min Medium was removed as above. Cells were lysed by adding 100 μl ice cold cell lysis buffer on ice and resuspending by pipetting ca. 5×. The plates were centrifuged at 3000 rpm for 10 min at 4° C. and 80 μl supernatant (or aliquots) were transferred into fresh polypropylene plates, shock-frozen in LN2, and stored at −80° C. until assayed.

AKT1,2(phospho-Ser473) EIA Kit Assay Designs #900-162: Samples (1:10 diluted) were added to the plate coated with a mouse MAB specific for the N-terminus of AKT and incubated 1 h at room temperature (RT) with shaking. The plates were washed 5×, incubated with biotinylated anti-phospho-AKT(Ser473) for 1 h at RT with shaking. The plates were then washed 5× and incubated with streptavidin-HRP conjugate 30 min at RT with shaking. The plates were then washed 5×, incubated with TMB substrate for 30 minutes at RT with shaking. The assays were stopped and read at 450 nm.

Mab 205.10.2 showed an IC50 of the AKT phosphorylation inhibition of 0.06 μg/ml.

In an pAKT ELISA in MeI-Juso cell performed as described for MCF7 cells Mab 205.10.2 showed an IC50 of AKT phosphorylation inhibition of 0.28 μg/ml all the other analyses antibodies show an IC50 above (>) 50.

% AKT phosporylation inhibition in Mel-Juso cells

| Antibody | IC50 [μg/ml] |
|---|---|
| Mab 205.10.2 | 0.28 |
| 105.5 (α-HER$^{ECD}$) | 0.81 |
| 1B4C3 | >50 |
| 2D1D12 | >50 |
| 8B8D9 | >50 | c) Inhibition of Tumor Cell Proliferation

The anti-tumor efficacy of HER3 antibodies Mab205.10.1, Mab205.10.2, and Mab205.10.3 in a cell proliferation assay, using MDA-MB-175 cells (VII Human Breast Carcinoma Cells, ATCC catalog no. HTB-25), was assessed. 20,000 cells per well were seeded into sterile 96 well tissue culture plates with DMEM/F12 cell culture medium, containing 10% FCS and incubated at 37° C.±1° C. with 5%±1% $CO_2$ for one day. The cells are slow growing cells with a doubling time of ca. 1.5 days. Anti-HER3 antibodies were added in dilution series and further incubated for 6 days. Cell viability was then assessed using the alamarBlue® readout. If the cell viability was reduced to more than 50% of control, IC50 values were calculated using means of triplicates for each antibody concentration; otherwise, if the % inhibition of cell viability at the highest concentration was below 50%, no IC50 could be calculated and it is indicated that $IC_{50}$ [μg/ml] is above (>) the highest concentration. Also the anti-HER3-antibodies U1-59 described in WO 2007/077028 and Ab#6 described in WO 2008/100624 were investigated.

| antibody | $IC_{50}$ [μg/ml] |
|---|---|
| Mab205.10.1 | 8.0 |
| Mab205.10.2 | 3.8 |
| Mab205.10.3 | 6.8 |
| U1-59 | 12.4 |
| Ab#6 | >60 μg/ml |

In a further experiment the anti-HER3 antibodies 8B8.2D9 described in WO 97/35885, and 1B4C3 described in WO 2003/013602 were investigated.

| antibody | $IC_{50}$ [μg/ml] |
|---|---|
| 8B8.2D9 | >100 μg/ml (29% inhibition at 100 μg/ml) |
| 1B4C3 | >100 μg/ml (26% inhibition at 100 μg/ml) |

Example 5

In Vitro ADCC in KPL-4 Tumor Cells

The target cells KPL4 (ADCC), breast carcinoma, cultivated in RPMI1640+2 mM L-alanyl-L-Glutamine+10% FCS) were collected with trypsin/EDTA (Gibco #25300-054)

in exponential growth phase. After a washing step and checking cell number and viability, the aliquot needed was labeled for 30 min at 37° C. in the cell incubator with calcein (Invitrogen #C3100MP; 1 vial was resuspended in 50 μl DMSO for 5 Mio cells in 5 ml medium). Afterwards, the cells were washed three times with AIM-V medium, the cell number and viability was checked and the cell number adjusted to 0.3 Mio/ml.

Meanwhile, PBMC (Peripheral Blood Mononuclear Cells) as effector cells were prepared by density gradient centrifugation (Histopaque-1077, Sigma # H8889) according to the manufacturer's protocol (washing steps 1× at 400 g and 2× at 350 g 10 min each). The cell number and viability was checked and the cell number adjusted to 15 Mio/ml.

100 μl calcein-stained target cells were plated in round-bottom 96-well plates, 50 μl diluted, afucosylated antibody (Mab205.10.1, Mab205.10.2, Mab205. 10.3, preparation see below) which was added and 50 μl effector cells. In some experiments the target cells were mixed with Redimune® NF Liquid (ZLB Behring) at a concentration of 10 mg/ml Redimune.

As a control for spontaneous lysis, target and effector cells were co-cultured without antibody and the maximal lysis was determined by 1% Triton X-100 lysis of target cells only. The plate was incubated for 4 hours at 37° C. in a humidified cell incubator.

The killing of target cells was assessed by measuring LDH (Lactate Dehydrogenase) release from damaged cells using the Cytotoxicity Detection kit (LDH Detection Kit, Roche #1 644 793) according to the manufacturer's instruction. Briefly, 100 μl supernatant from each well was mixed with 100 μl substrate from the kit in a transparent flat bottom 96 well plate. The Vmax values of the substrate's colour reaction was determined in an ELISA reader at 490 nm for at least 10 min. Percentage of specific antibody-mediated killing was calculated as follows: $((A-SR)/(MR-SR) \times 100)$, where A is the mean of Vmax at a specific antibody concentration, SR is the mean of Vmax of the spontaneous release and MR is the mean of Vmax of the maximal release.

As an additional readout, the calcein retention of intact target cells was assessed by lysing the remaining target cells in borate buffer (5 mM sodium borate+0.1% Triton) and measuring the calcein fluorescence in a fluorescence plate reader. Mab205.10.1, Mab205.10.2, Mab205.10.3 showed and ADCC [KPL-4] by 1 μg/ml of specific Lysis of about 40-60%.

The afucosylated antibody (Mab205.10.1, Mab205.10.2, Mab205.10.3) were prepared by co-transfection with four plasmids, two for antibody expression, one for a fusion GnTIII polypeptide expression (a GnT-III expression vector), and one for mannosidase II expression (a Golgi mannosidase II expression vector) at a ratio of 4:4:1:1, respectively in HEK293 or CHO cells.

The full antibody heavy and light chain DNA sequences were subcloned into mammalian expression vectors (one for the light chain and one for the heavy chain) under the control of the MPSV promoter and upstream of a synthetic polyA site, each vector carrying an EBV OriP sequence. Antibodies were produced by co-transfecting HEK293-EBNA cells or CHO cells with the antibody heavy and light chain expression vectors using a calcium phosphate-transfection approach. Exponentially growing HEK293-EBNA cells were transfected by the calcium phosphate method. For the production of the glycoengineered antibody, the cells were co-transfected with four plasmids, two for antibody expression, one for a fusion GnTIII polypeptide expression (a GnT-III expression vector), and one for mannosidase II expression (a Golgi mannosidase II expression vector) at a ratio of 4:4:1:1, respectively. Cells were grown as adherent monolayer cultures in T flasks using DMEM culture medium supplemented with 10% FCS, and were transfected when they were between 50 and 80% confluent. For the transfection of a T150 flask, 15 million cells were seeded 24 hours before transfection in 25 ml DMEM culture medium supplemented with FCS (at 10% V/V final), and cells were placed at 37° C. in an incubator with a 5% CO2 atmosphere overnight. For every antibody to be produced, a solution of DNA, CaCl2 and water was prepared by mixing 188 μg total plasmid vector DNA (four plasmids, two for antibody expression (one light chain and one heavy chain), one for a fusion GnTIII polypeptide expression (a GnT-III expression vector), and one for mannosidase II expression (a Golgi mannosidase II expression vector) at a ratio of 4:4:1:1, respectively), water to a final volume of 938 μl and 938 μl of a 1M CaCl2 solution. To this solution, 1876 μl of a 50 mM HEPES, 280 mM NaCl, 1.5 mM Na2HPO4 solution at pH 7.05 were added, mixed immediately for 10 sec and left to stand at room temperature for 20 sec. The suspension was diluted with 46 ml of DMEM supplemented with 2% FCS, and divided into two T150 flasks in place of the existing medium. The cells were incubated at 37° C., 5% CO2 for about 17 to 20 hours, then medium was replaced with 25 ml DMEM, 10% FCS. The conditioned culture medium was harvested 7 days post-transfection by centrifugation for 15 min at 210×g, the solution was sterile filtered (0.22 μm filter) and sodium azide in a final concentration of 0.01% w/v was added, and kept at 4° C.

The secreted afucosylated antibodies were purified and the oligosaccharides attached to the Fc region of the antibodies were analysed e.g. by MALDI/TOF-MS (as described in e.g. WO 2008/077546). For this analysis oligosaccharides were enzymatically released from the antibodies by PNGaseF digestion, with the antibodies being either immobilized on a PVDF membrane or in solution. The resulting digest solution containing the released oligosaccharides was either prepared directly for MALDI/TOF-MS analysis or was further digested with EndoH glycosidase prior to sample preparation for MALDI/TOF-MS analysis. The analyzed amount of fucose within the sugar chain at Asn297 was between 50-20%.

Example 6

In Vivo Antitumor Efficacy

The in vivo antitumor efficacy of the antibodies Mab205.10.1, Mab205.10.2, Mab205.10.3 could be detected in cell and fragment based models of various tumor origin (e.g. lung cancer, SCCHN, breast- and pancreatic cancer) transplanted on SCID beige or nude mice. As examples data are shown for the SCCHN xenograft model FaDu (cell line based), breast cancer model MAXF449 (fragment-based) and NSCLC model 7177 (fragment-based).

Test Agents

Afucosylated Mab205.10.2 (designated Mab 205 in FIGS. 2, 3, 4) was provided as stock solution from Roche, Penzberg, Germany. Antibody buffer included histidine. Antibody solution was diluted appropriately in buffer from stock prior injections.

Cell Lines and Culture Conditions

FaDu human HNSCC cells were originally obtained from ATCC. The tumor cell line was routinely cultured in MEM Eagle medium supplemented with 10% fetal bovine serum, 2 mM L-glutamine, 1 mM sodium pyruvate and 0.1 mM NEAA at 37° C. in a water-saturated atmosphere at 5% $CO_2$. Culture passage was performed with trypsin/EDTA 1× splitting every third day.

Tumor Fragments

Tumor fragments were originally taken from patients and transplanted s.c. to nude donor mice. Subsequently tumor fragments are serial passaged in vivo. For a preclinical study small tumor fragments were generated from donor mice and placed s.c. on further nude mice (MAXF449, 7177).

Animals

Female SCID beige or nude mice were purchased from breeder (e.g. Charles River, Sulzfeld, Germany) and maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum.

Monitoring

Animals were controlled daily for clinical symptoms and detection of adverse effects. For monitoring throughout the experiment body weight of animals was documented.

Treatment of Animals

Animal treatment started after animal randomisation after cell or fragment transplantation when median tumor size was about 100-150 $mm^3$ Antibody was administered as single agent at 10 or 25 mg/kg i.p. q7d once weekly for 3-6 weeks depending of the model. The corresponding vehicle was administered on the same days.

Antibody Efficacy

A) FaDu HNSCC Xenograft

FaDu HNSCC xenograft bearing mice were treated with antibody Mab205.10.2 from study day 14 to 35. As a result, treatment with the Mab205.10.2 antibody showed significant anti-tumor efficacy with tumors stasis of s.c. FaDu xenografts. The Tumor Growth Inhibition (TGI) was calculated at 98%.

Figure 2:
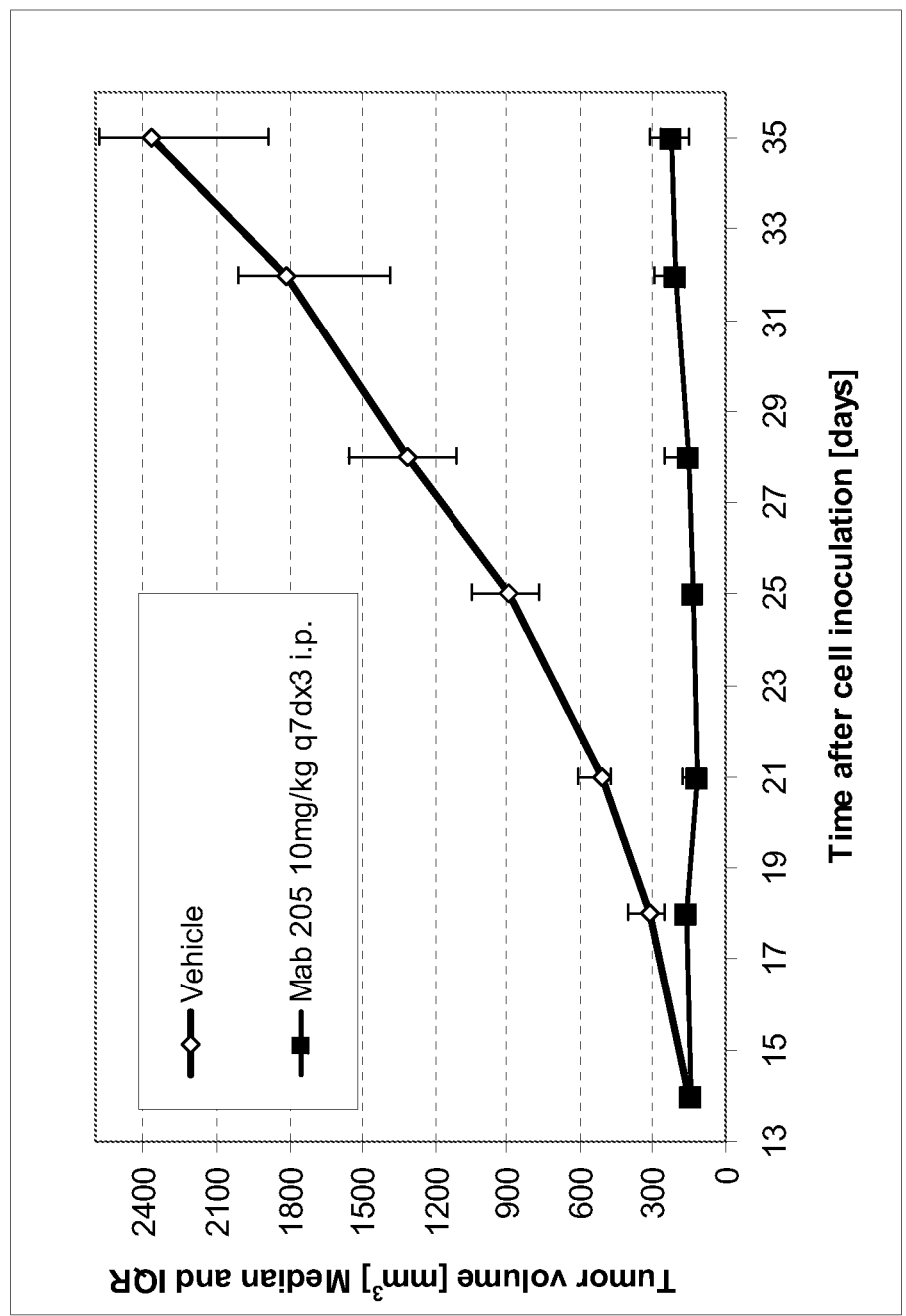

Treatment with Mab 205 (10 mg/kg q7dx3, i.p.) resulted in tumor stasis of FaDu SCCHN transplanted xenografts (see FIG. 2).

B) MAXF449 Breast Cancer Xenograft

MAXF449 breast cancer xenograft bearing mice were treated with antibody Mab205.10.2 from study day 64 to 91, As a result, treatment with the Mab205.10.2 antibody showed significant anti-tumor efficacy with tumors stasis of MAXF449 xenografts. The Tumor Growth Inhibition (TGI) was over 100%.

Figure 3:
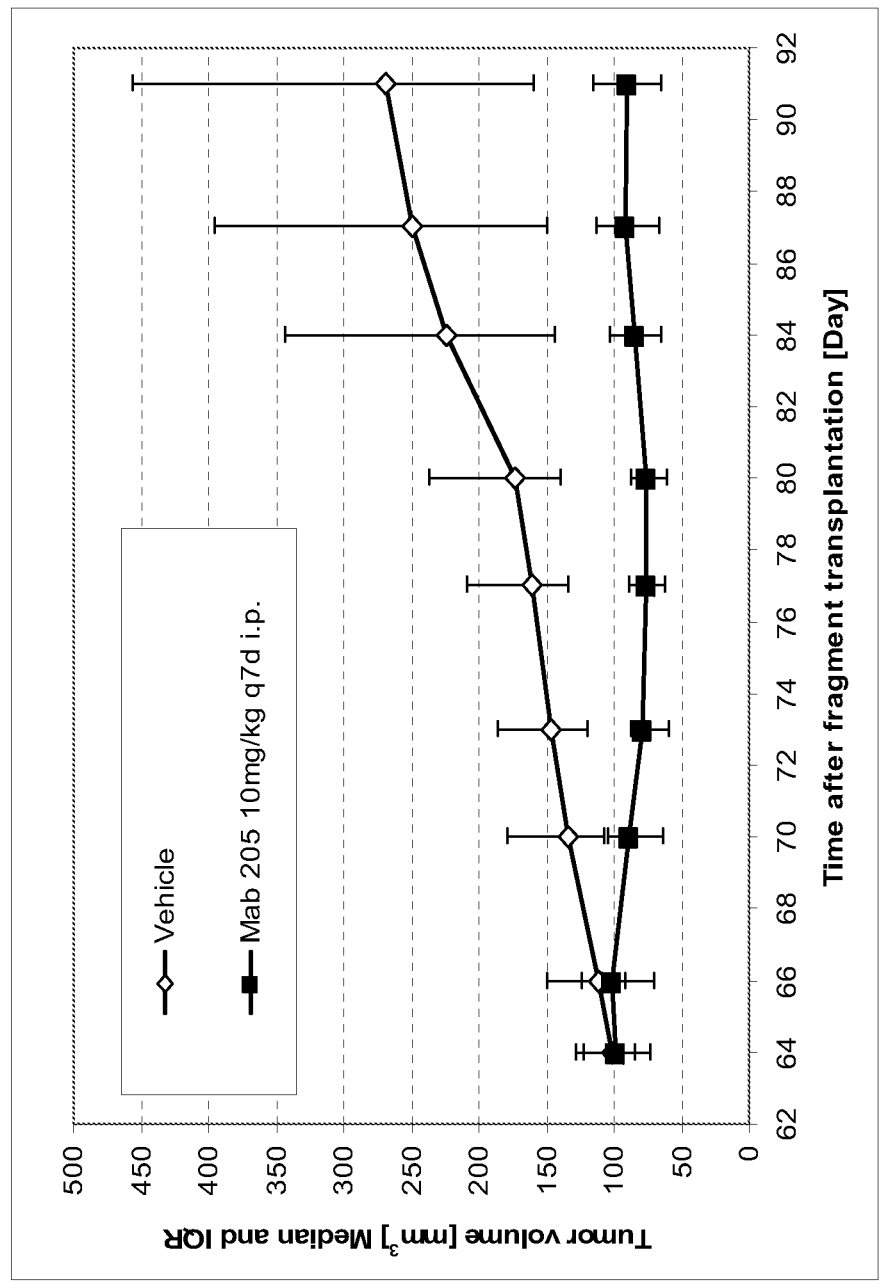

Treatment with Mab 205 (10 mg/kg q7d, i.p.) resulted in tumor stasis of MAXF449 breast cancer transplanted xenografts (see FIG. 3).

C) 7177 NSCLC Xenograft

7177 NSCLC xenograft bearing mice were treated with antibody Mab205.10.2 from study day 28 to 56. As a result, treatment with the Mab205.10.2 antibody showed significant anti-tumor efficacy with tumors stasis of 7177 NSCLC xenografts. The Tumor Growth Inhibition (TGI) was over 100%.

Figure 4:
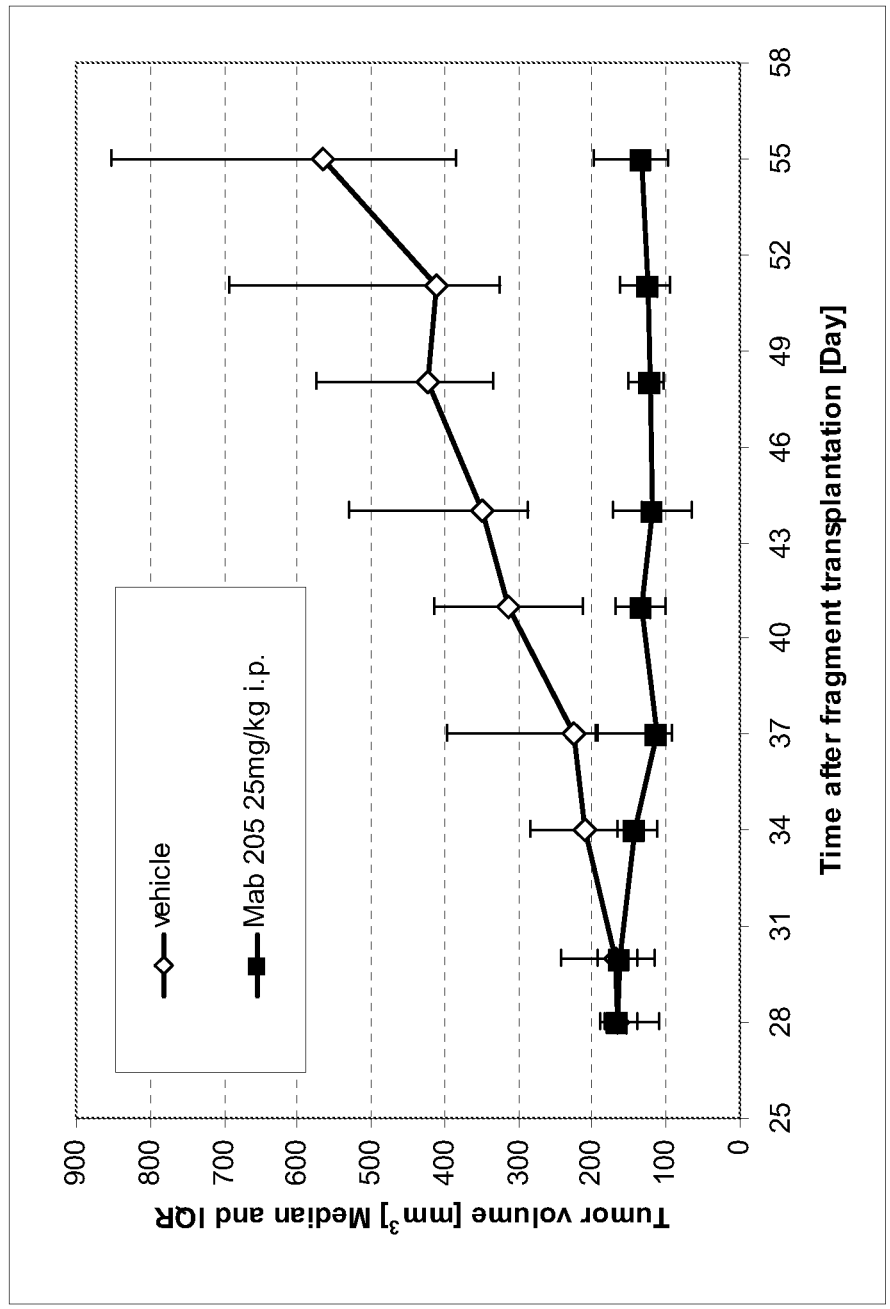

Treatment with Mab 205 (25 mg/kg q7d, i.p.) resulted in tumor stasis of 7177 NSCLC transplanted xenografts (see FIG. 4).

We claim:

1. An isolated antibody which binds to human HER3, wherein the antibody comprises a heavy chain variable domain VH comprising the amino acid sequence of SEQ ID NO:8; and a light chain variable domain VL comprising the amino acid sequence of SEQ ID NO:10.

2. The antibody according to claim 1, wherein the antibody is a humanized antibody.

3. The antibody according to claim 1, wherein the antibody is of IgG4 subclass.

4. The antibody according to claim 1, wherein the antibody is of IgG1 subclass.

5. The antibody according to claim 4, wherein the antibody is glycosylated with a sugar chain at Asn297 whereby the amount of fucose within said sugar chain is 65% or lower.

6. The antibody of claim 5, wherein the amount of fucose within said sugar chain is between 5% and 65.

7. The antibody of claim 5, wherein the amount of fucose within said sugar chain is between 5% and 65%.

* * * * *

SEQUENCE LISTING

```
<160> NUMBER OF SEQ ID NOS: 17

<210> SEQ ID NO 1
<211> LENGTH: 11
<212> TYPE: PRT
<213> ORGANISM: Artificial
<220> FEATURE:
<223> OTHER INFORMATION: heavy chain CDR3H, Mab 205.10

<400> SEQUENCE: 1

His Arg Asp Tyr Tyr Ser Asn Ser Leu Thr Tyr
1               5                   10

<210> SEQ ID NO 2
<211> LENGTH: 17
<212> TYPE: PRT
<213> ORGANISM: Artificial
<220> FEATURE:
<223> OTHER INFORMATION: heavy chain CDR2H, Mab 205.10

<400> SEQUENCE: 2

Trp Ile Ser Ala Tyr Asn Gly Asn Thr Asn Tyr Ala Gln Lys Leu Gln
1               5                   10                  15

Gly

<210> SEQ ID NO 3
<211> LENGTH: 10
<212> TYPE: PRT
<213> ORGANISM: Artificial
<220> FEATURE:
<223> OTHER INFORMATION: heavy chain CDR1H, Mab 205.10
```

```
<400> SEQUENCE: 3

Gly Tyr Thr Phe Arg Ser Ser Tyr Ile Ser
1               5                   10

<210> SEQ ID NO 4
<211> LENGTH: 9
<212> TYPE: PRT
<213> ORGANISM: Artificial
<220> FEATURE:
<223> OTHER INFORMATION: light chain CDR3L, Mab 205.10

<400> SEQUENCE: 4

Gln Ser Asp Tyr Ser Tyr Pro Tyr Thr
1               5

<210> SEQ ID NO 5
<211> LENGTH: 7
<212> TYPE: PRT
<213> ORGANISM: Artificial
<220> FEATURE:
<223> OTHER INFORMATION: light chain CDR2L, Mab 205.10

<400> SEQUENCE: 5

Trp Ala Ser Thr Arg Glu Ser
1               5

<210> SEQ ID NO 6
<211> LENGTH: 17
<212> TYPE: PRT
<213> ORGANISM: Artificial
<220> FEATURE:
<223> OTHER INFORMATION: light chain CDR1L (variant 1), Mab 205.10

<400> SEQUENCE: 6

Lys Ser Ser Gln Ser Leu Leu Asn Ser Gly Asn Gln Lys Asn Tyr Leu
1               5                   10                  15

Thr

<210> SEQ ID NO 7
<211> LENGTH: 17
<212> TYPE: PRT
<213> ORGANISM: Artificial
<220> FEATURE:
<223> OTHER INFORMATION: light chain CDR1L (variant 2), Mab 205.10

<400> SEQUENCE: 7

Lys Ser Ser Gln Ser Val Leu Asn Ser Gly Asn Gln Lys Asn Tyr Leu
1               5                   10                  15

Thr

<210> SEQ ID NO 8
<211> LENGTH: 120
<212> TYPE: PRT
<213> ORGANISM: Artificial
<220> FEATURE:
<223> OTHER INFORMATION: heavy chain variable domain VH, Mab 205.10

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45
```

```
Gly Trp Ile Tyr Ala Gly Thr Gly Ser Pro Ser Tyr Asn Gln Lys Leu
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg His Arg Asp Tyr Tyr Ser Asn Ser Leu Thr Tyr Trp Gly Gln
             100                 105                 110

Gly Thr Leu Val Thr Val Ser Ser
         115                 120

<210> SEQ ID NO 9
<211> LENGTH: 113
<212> TYPE: PRT
<213> ORGANISM: Artificial
<220> FEATURE:
<223> OTHER INFORMATION: light chain variable domain VL, Mab 205.10.1

<400> SEQUENCE: 9

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Ser
                 85                  90                  95

Asp Tyr Ser Tyr Pro Tyr Thr Phe Gly Gln Gly Thr Lys Leu Glu Ile
             100                 105                 110

Lys

<210> SEQ ID NO 10
<211> LENGTH: 113
<212> TYPE: PRT
<213> ORGANISM: Artificial
<220> FEATURE:
<223> OTHER INFORMATION: light chain variable domain VL, Mab 205.10.2

<400> SEQUENCE: 10

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Ser
                 85                  90                  95

Asp Tyr Ser Tyr Pro Tyr Thr Phe Gly Gln Gly Thr Lys Leu Glu Ile
             100                 105                 110
```

Lys

<210> SEQ ID NO 11
<211> LENGTH: 113
<212> TYPE: PRT
<213> ORGANISM: Artificial
<220> FEATURE:
<223> OTHER INFORMATION: light chain variable domain VL, Mab 205.10.3

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ser Ile Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys

<210> SEQ ID NO 12
<211> LENGTH: 107
<212> TYPE: PRT
<213> ORGANISM: Homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 330
<212> TYPE: PRT
<213> ORGANISM: Artificial
<220> FEATURE:
<223> OTHER INFORMATION: human heavy chain constant region derived from
      IgG1 mutated on L234A and L235A

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro

```
                100                 105                  110
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 16
<211> LENGTH: 327
<212> TYPE: PRT
<213> ORGANISM: Artificial
<220> FEATURE:
<223> OTHER INFORMATION: human heavy chain constant region derived from
      IgG4 mutated onS228P

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125
```

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 17
<211> LENGTH: 1342
<212> TYPE: PRT
<213> ORGANISM: homo sapiens

<400> SEQUENCE: 17

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
        50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

-continued

```
Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
            580                 585                 590
```

-continued

```
Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
        610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu  Glu Glu Val Glu Leu  Glu Pro Glu
        995                 1000                1005

Leu Asp  Leu Asp Leu Asp Leu  Glu Ala Glu Glu Asp  Asn Leu Ala
```

```
         1010               1015                 1020
Thr Thr  Thr Leu Gly Ser Ala Leu Ser Leu Pro Val Gly Thr Leu
         1025               1030                 1035

Asn Arg  Pro Arg Gly Ser Gln Ser Leu Leu Ser Pro Ser Ser Gly
         1040               1045                 1050

Tyr Met  Pro Met Asn Gln Gly Asn Leu Gly Glu Ser Cys Gln Glu
         1055               1060                 1065

Ser Ala  Val Ser Gly Ser Ser Glu Arg Cys Pro Arg Pro Val Ser
         1070               1075                 1080

Leu His  Pro Met Pro Arg Gly Cys Leu Ala Ser Glu Ser Ser Glu
         1085               1090                 1095

Gly His  Val Thr Gly Ser Glu Ala Glu Leu Gln Glu Lys Val Ser
         1100               1105                 1110

Met Cys  Arg Ser Arg Ser Arg Ser Arg Ser Pro Arg Pro Arg Gly
         1115               1120                 1125

Asp Ser  Ala Tyr His Ser Gln Arg His Ser Leu Leu Thr Pro Val
         1130               1135                 1140

Thr Pro  Leu Ser Pro Pro Gly Leu Glu Glu Asp Val Asn Gly
         1145               1150                 1155

Tyr Val  Met Pro Asp Thr His Leu Lys Gly Thr Pro Ser Ser Arg
         1160               1165                 1170

Glu Gly  Thr Leu Ser Ser Val Gly Leu Ser Ser Val Leu Gly Thr
         1175               1180                 1185

Glu Glu  Glu Asp Glu Asp Glu Glu Tyr Glu Tyr Met Asn Arg Arg
         1190               1195                 1200

Arg Arg  His Ser Pro Pro His Pro Pro Arg Pro Ser Ser Leu Glu
         1205               1210                 1215

Glu Leu  Gly Tyr Glu Tyr Met Asp Val Gly Ser Asp Leu Ser Ala
         1220               1225                 1230

Ser Leu  Gly Ser Thr Gln Ser Cys Pro Leu His Pro Val Pro Ile
         1235               1240                 1245

Met Pro  Thr Ala Gly Thr Thr Pro Asp Glu Asp Tyr Glu Tyr Met
         1250               1255                 1260

Asn Arg  Gln Arg Asp Gly Gly Gly Pro Gly Gly Asp Tyr Ala Ala
         1265               1270                 1275

Met Gly  Ala Cys Pro Ala Ser Glu Gln Gly Tyr Glu Glu Met Arg
         1280               1285                 1290

Ala Phe  Gln Gly Pro Gly His Gln Ala Pro His Val His Tyr Ala
         1295               1300                 1305

Arg Leu  Lys Thr Leu Arg Ser Leu Glu Ala Thr Asp Ser Ala Phe
         1310               1315                 1320

Asp Asn  Pro Asp Tyr Trp His Ser Arg Leu Phe Pro Lys Ala Asn
         1325               1330                 1335

Ala Gln  Arg Thr
         1340
```